United States Patent [19]

Mihara et al.

[11] Patent Number: 5,962,305
[45] Date of Patent: Oct. 5, 1999

[54] MICROBIAL STRAIN, METHOD FOR BIODEGRADING ORGANIC COMPOUNDS AND METHOD FOR ENVIRONMENTAL REMEDIATION

[75] Inventors: Chieko Mihara, Isehara; Tetsuya Yano, Atsugi; Shinya Kozaki, Tokyo; Takeshi Imamura, Chigasaki, all of Japan

[73] Assignee: Canon Kabushiki Kaisha, Tokyo, Japan

[21] Appl. No.: 08/904,018

[22] Filed: Jul. 31, 1997

[30] Foreign Application Priority Data

Aug. 1, 1996 [JP] Japan .................... 8-203666

[51] Int. Cl.⁶ ............... B09B 3/00; C12N 1/20
[52] U.S. Cl. ................... 435/262.5; 435/252.1; 435/253.3
[58] Field of Search ............ 435/262.5, 252.1, 435/253.3

[56] References Cited

U.S. PATENT DOCUMENTS

| | | | |
|---|---|---|---|
| 4,877,736 | 10/1989 | Fliermans | 435/183 |
| 4,925,802 | 5/1990 | Nelson et al. | 435/262 |
| 5,079,166 | 1/1992 | Winter | 435/262 |
| 5,658,795 | 8/1997 | Kato et al. | 435/262.5 |
| 5,665,597 | 9/1997 | Imamura et al. | |
| 5,679,568 | 10/1997 | Imamura et al. | |

FOREIGN PATENT DOCUMENTS

| | | |
|---|---|---|
| 2-92274 | 4/1990 | Japan . |
| 2-503866 | 11/1990 | Japan . |
| 3-292970 | 12/1991 | Japan . |
| 4-502277 | 4/1992 | Japan . |
| 6-22769 | 2/1994 | Japan . |
| 6-70753 | 3/1994 | Japan . |
| 6-105691 | 4/1994 | Japan . |
| 7-123976 | 5/1995 | Japan . |
| 7-236895 | 9/1995 | Japan . |
| 8-294387 | 11/1996 | Japan . |
| WO92-19738 | 11/1992 | WIPO . |

OTHER PUBLICATIONS

Vandenbergh et al., "Metabolism of volatile chlorinated aliphatic hydrocarbons by *Pseudomonas fluorescens*" 1988, vol. 54, No. 10, pp. 2578–2579.
Gibson D.T. "Assay of enzymes of aromatic metabolism", In: Methods in Microbiology, 1997, vol. 6B, chapter XI, pp. 463–468.
Bergey's Manual of Determinative Bacteriology, Ninth Edition, 1994, pp. 151–157.
Munakata Marr et al., "Enchancement of trichloroethylene degradation in aquifer microcosms bioaugmented with wild type and geneticaly alsterd *Burkholderia* (*Pseudomonas*) *cepacis* G4 and PR1", Environ.Sci.Technol. 1996, 30, pp. 2045–2052.
Uchiyama, et al. "Aerobic Degradation of Trichloroethylene . . . Strain M", Agric. Biol. Chem. 53 (11), 2903–2907, 1989.
Negoro, et al. Growth of Microalgae . . . and $NO_x$, Appl. Biochem. & Biotech., 28/29, 877–886 (1991).
Tsien, et al. "Biodegradation of Trichloroethelene by . . . OB3b", Appl. Environ. Microbiol., 55, (12), 3155–3161 (1989).
Henry, et al.; "Influence of Endogenous and Exogenous . . . Aquifier", Appl. & Environ. Microbiol., 57, (1), 236–244 (1991).
Harker, et al.; "Trichloroethylene Degradation . . . JMP134", Appl. & Environ. Microbiol., 56, (4), 1179–1181 (1990).
Wackett, et al., "Survey of Microbiol. Oxygenases: . . . Bacteria", Appl. & Environ. Microbiol., 55, (11), 2960–2964 (1989).
Nelson, et al., "Aerobic Metabolism of Trichloroethylene . . . Isolate", Appl. & Environ. Microbiol., 52, (2), 383–384 (1986).
Nelson, et al., "Biodegradation of Trichloroethylene . . . Pathway", Appl. & Environ. Microbiol., 53, (5), 949–954 (1987).
Little, et al., "Trichloroethylene Biodegradation . . . Bacterium", Appl. & Environ. Microbiol., 54, (4), 951–956 (1988).
Kamath, et al., "New Pathway for the Biodegradation . . . niger", Appl. & Environ. Microbiol., 56, (1), 275–280 (1990).
Sandt, et al., "Mobilization of the genetically . . . Drinking Water", Appl. & Environ. Microbiol., 57, (1), 194–200 (1991).
Wackett, et al., "Degradation of Trichloroethylene . . . F1", Appl. & Environ. Microbiol., 54, (1), 1703–1708 (1988).
Vannelli, et al., "Degradation of Halogenated . . . *Nitrosomonas europaea*", Appl. & Environ. Microbiol., 56, (4), 1169–1171 (1990).
Shields, et al., "Selection of a *Pseudomaonas cepacia* . . . Trichloroethelene", Appl. & Environ. Microbiol., 58, (12), 3977–3982 (1992).
Ewers, et al., "Selection of trichloroethene (TCE) . . . by TCE", Arch. Microbiol., 154, (4), 410–413 (1990).
Nakajima, et al., "Novel Metabolite of Trichloroethylene . . . Pathway", Biosci. Biotech. Biochem., 56, (3), 486–489 (1992).
Nakajima, et al., "Purification and Properties . . . Methylocystis", Biosci. Biotech. Biochem., 56, (5), 736–740 (1992).
Int. J. Systm. Bact., 39, (3), 369–70 (1989).

(List continued on next page.)

*Primary Examiner*—Irene Marx
*Assistant Examiner*—Vera Afremova
*Attorney, Agent, or Firm*—Fitzpatrick, Cella, Harper & Scinto

[57] ABSTRACT

A novel microbial strain JMC1 (FERM BP-5960) that it is a mutant strain derived from JM1 (FERM BP-5352) constitutively expressing oxygenase, and a method for biodegrading aromatic compounds and chlorinated organic compounds by using strain JMC1 as well as a method for environmental remediation which comprises a step of biodegrading contaminant in the environment by using strain JMC1. Aromatic compounds and/or chlorinated aliphatic hydrocarbon compounds contained in the environment can be removed at a low temperature by using the novel strain JMC1 without using any inducer substances.

25 Claims, 14 Drawing Sheets

OTHER PUBLICATIONS

Winter, et al., "Efficient Degradation of Trichloroethylene . . . Coli", Bio/Technology, 7, pp. 282–285 (1989).

Beam, et al., "Microbial Degradation of . . . Commensalism", J. Gen. Microbiol., 82, 163–169 (1974).

Hanson, et al., "Development of Methanotrophs . . . Chlorinated Olefins", Preprinted Extended Abstract, Div. Env. Chem., A.C.S. Miami Beach, Fla., pp. 365–367, Sep. 10–15, 1989.

Journal of Japan Sewage Works Assoc., 24, 273, 27–32 (1987).

MICROBIAL STRAIN, METHOD FOR BIODEGRADING ORGANIC COMPOUNDS AND METHOD FOR ENVIRONMENTAL REMEDIATION

BACKGROUND OF THE INVENTION

1. Field of the Invention

This invention relates to a novel microbial strain and a method of biodegrading chlorinated organic compounds such as trichloroethylene (TCE) and dichloroethylene (DCE) by using it. It also relates to a method of environmental remediation by treating aqueous media such as drain water and waste aqueous solutions containing chlorinated organic compounds. Such a method is useful for recovering the soil and the air (gaseous phase of the environment) from contamination particularly when the air is contaminated by chlorinated organic compounds.

2. Related Background Art

In recent years, environmental contamination by hardly decomposable chlorinated organic compounds that are harmful to living things has been a major environmental problem. Particularly, it is assumed that the soil of industrial zones relating to paper manufacturing, pulp industry and precision machining has been contaminated to a large extent by chlorinated organic compounds including chlorinated aliphatic hydrocarbon compounds such as tetrachloroethylene (PCE), trichloroethylene (TCE) and dichloroethylene (DCE) and this assumption has been justified by a number of reports on the environment of industrial quarters around the world. The chlorinated organic compounds discharged into soil are then dissolved into underground water and spread to surrounding areas to contaminate them. Most of these compounds are strongly suspected to be carcinogenic and provide a major social problem particularly because many people are relying on underground water for water supply and these compounds are highly stable in the environment.

Under these circumstances, it is of vital importance from the viewpoint of environmental protection to treat contaminated aqueous media such as underground water, soil and the surrounding gaseous phase by removing and degrading the chlorinated organic compounds contained therein and, in fact, efforts have been paid to develop technologies necessary for such treatment operations.

While known technologies for environmental protection include adsorption using active carbon and degradation by heat or light, they are not necessarily viable and feasible in terms of cost and operability.

Meanwhile, microorganisms that degrade chlorinated organic compounds such as TCE that are normally stable in the environment have been reported and a number of researches have been started to exploit them in practical applications. Some of the advantages of using microorganisms for biodegradation processes are that chlorinated organic compounds can be reduced harmless by appropriately selecting one or more specific microorganisms and using them for biodegradation, that basically no chemicals are required for biodegradation and that the cost of maintenance and labor force can be lessened in biodegradation processes. However, there is a limited number of reports on isolated microorganisms having the ability of degrading chlorinated organic compounds. Known microbial strains that can be used for the biodegradation of TCE include *Welchia alkenophila* sero 5 (U.S. Pat. No. 4,877,736, ATCC 53570), *Welchia alkenophila* sero 33 (U.S. Pat. No. 4,877,736, ATCC 53571), Methylocystis sp. strain M (Agric Biol. Chem., 53, 2903 (1989), Biosci. Biotech. Biochem., 56, 486 (1992), ibid 56, 736 (1992)), *Methylosinus trichosporium* OB3b (Am. Chem. Soc. Natl. Meet. Dev. Environ. Microbiol., 29, 365 (1989), Appl. Environ. Microbiol., 55, 3155 (1989), Appl. Biochem. Biotechnol., 28, 877 (1991), Japanese Laid-Open Patent Application No. 2-92274, Japanese Patent Application Laid-Open No. 3-292970), Methylomonas sp. MM2 (Appl. Environ. Microbiol., 57, 236 (1991)), *Alcaligenes denitrificans* ssp. xylosoxidans JE75 (Arch. Microbiol., 154, 410 (1990)), *Alcaligenes eutrophus* JMP134 (Appl. Environ. Microbiol., 56, 1179 (1990)), *Alcaligenes eutrophus* FERM-13761 (Japanese Patent Application Laid-Open No. 7-123976), *Pseudomonas aeruginosa* JI104 (Japanese Patent Application Laid-Open No. 7-236895), *Mycobacterium vaccae* JOB5 (J. Gen. Microbiol., 82, 163 (1974), Appl. Environ. Microbiol., 55, 2960, (1989), ATCC 29678), *Pseudomonas putida* BH (J. of Japan Sewage Work Assoc. (Gesuido Kyokai-shi), 24, 27 (1987), Pseudomonas sp. strain G4 (Appl. Environ. Microbiol., 52, 383, (1986), ibid 53, 949 (1987), ibid 54, 951 (1989), ibid 56, 279 (1990), ibid 57, 193 (1991), U.S. Pat. No. 4,925,802, ATCC 53617, this strain was first classified as *Pseudomonas cepacia* but later changed to Pseudomonas sp.), *Pseudomonas mendocina* KR-1 (Bio/Technol., 7, 282 (1989), *Pseudomonas putida* F1 (Appl. Environ. Microbiol., 54, 1703 (1988), ibid 54, 2578 (1988)), *Pseudomonas fluorescens* PFL12 (Appl. Environ. Microbiol., 54, 2578 (1988)), *Pseudomonas putida* KWI-9 (Japanese Patent Application Laid-Open No. 6-70753), *Pseudomonas cepacia* KKO1 (Japanese Patent Application Laid-Open No. 6-22769), *Nitrosomonas europaea* (Appl. Environ. Microbiol., 56, 1169 (1990)) and *Lactobacillus vaginalis* sp. nov (Int. J. Syst. Bacteriol., 39, 368 (1989), ATCC 49540).

A problem in practically applying these decomposing bacteria for remedying the environment is that they require chemicals such as aromatic compounds or methane as an induction substance (an inducer).

While aromatic compounds such as phenol and toluene serve excellently as degradation inducers, they are toxic and should not be released into the environment. While methane is also useful as a degradation inducer, it is highly inflammable and hence it is difficult and highly hazardous to discharge methane into the environment in a controlled manner.

Nelson at al. developed a method of using tryptophan, an amino acid, as a degradation inducer for biodegrading chlorinated organic compounds (Japanese Patent Application Laid-Open No. 4-502277). Although this method can avoid the toxicity and danger of the inducer itself to some extent, tryptophan is a very expensive compound, and complicatedness of introducing a specific substance into the environment with control is not still solved. Additionally, adding excess carbon and nitrogen source into the environment is also not preferable from the viewpoint of eutrophication. Furthermore, since such TCE decomposition enzymes are inducible enzymes, the enzymatic activity once induced is usually sustained for from only several hours to a day, requiring another induction after that, and there is a problem that decomposition of TCE is competitively inhibited by the presence of the inducing agents.

Currently, efforts have been made to introduce an plasmid having a DNA fragment encoding oxygenase or hydroxylase as a TCE decomposition enzyme into a host bacterium in order to express the TCE decomposition activity using a harmless inducer or to constitutively express it in the absence of any inducers. Microbial strains having such a DNA fragment include *Pseudomonas mendocina* KR-1

(Japanese Patent Application Laid-Open No. 2-503866), *Pseudomonas putida* KWI-9 (Japanese Patent Application Laid-Open No. 6-105691) and *Pseudomonas putida* BH (Summary of the Third Conference for the Studies on the Contamination of Underground Water and Soil and Preventive Measures (1994)).

However, these recombinant strains have various different problems including the use of highly expensive IPTG (isopropylthiogalactopyranoside) and an insufficient stability of the plasmid in the host microorganism. Additionally, releasing recombinant microorganisms into the environment is under certain regulations considering the public acceptance.

Shields et al. obtained a mutant strain of Pseudomonas sp. strain G4 capable of degrading TCE in the absence of an inducer (phenol or toluene) using a transposon (Appl. Environ. Microbiol., 58, 3977 (1992), PCT Application, International Publication W092/19738).

However, this mutant strain of G4 is not satisfactorily active in TCE degradation and has a problem of instability due to the transposon. Additionally, since the transposon itself contains an antibiotic resistance gene such as kanamycin resistance, there may be a potential hazard of a horizontal transmission to other microorganisms when the mutant strain is released into the environment.

In view of the above identified problems and other problems, the inventors of the present invention conducted a series of mutation experiments on the J1 strain (FERM BP-5102) by means of nitrosoguanidine and succeeded in obtaining a new strain JM1 (FERM BP-5352) capable of degrading volatile chlorinated organic compounds and aromatic compounds without requiring an inducer as disclosed in Japanese Patent Application Laid-Open No. 8-294387).

More specifically, strain JM1 (FERM BP-5352) was obtained by mutagenizing strain JI (FERM BP-5201; National Institute of Bioscience and Human-Technology, Agency of Industrial Science and Technology) using a chemical, nitrosoguanidine, without genetic manipulations. Strain JM1 does not require the use of an inducer such as phenol, toluene or cresol for degrading volatile chlorinated organic compounds including TCE.

As a microorganism which can degrade chlorinated aliphatic hydrocarbon compounds such as TCE without an inducer, there has been reported *Burkholderia* (*Pseudomonas*) *cepacia* $PR1_{301}$ (hereinafter referred to simply as $PR1_{301}$) in Environmental Science & Technology, Vol.30, No.6, 1986, pp.2045–2052.

From the viewpoint of treating waste solutions and soil containing TCE, the microorganism to be used for the treatment is required to have not only a TCE degradability but also the ability of growing and maintaining its degradation activity in the poor environment of waste solution or soil.

In the natural soil environment, unlike culture systems in laboratories, the optimization of the growth and degradation activity of a microorganism capable of degrading chlorinated organic compounds is quite difficult due to the various factors, such as temperature, moisture content, pH, oxygen content and other parameters of soil, so that there still exist a number of problems to be solved for successfully recovering the soil from contamination by means of microorganisms capable of degrading contaminants.

Among these parameters, temperature is very important because it directly affects the growth and the degradation activity of the microorganism introduced in the soil. The soil temperature in the Temperate Zone where Japan is located is held substantially constant to about 15° C., which is significantly lower than 25° C., the optimum temperature for the growth and decomposition activity of strain JM1. While strain JM1 can sufficiently grow and express its biodegradation activity around 15° C. in practical applications, the soil temperature near the surface may fall significantly from that level in winter in Japan where the ambient temperature may fall well below zero. In colder regions, such as cryic and frigid as defined by the Soil Taxonomy of the Department of Agriculture of the U.S. Government, the average annual soil temperature is between 0 and 8° C., and between 8 and 15° C. in mecic.

Therefore, there exists a need for a technology in order to fully exploit the excellent properties of strain JM1 for degrading aromatic compounds and/or chlorinated organic compounds without using an inducer, at a temperature typically between 4 and 15° C.

SUMMARY OF THE INVENTION

The object of the present invention is to provide a novel microbial strain that can remarkably degrade contaminants without an inducer in a low temperature zone and a method of degrading contaminants by using it, as well as a method of environmental remediation using it.

According to an aspect of the invention, there is provided a novel strain JMC1 (FERM BP-5960) constitutively expressing an oxygenase, which is a mutant strain derived from strain JM1 (FERM BP-5352).

According to another aspect of the invention, there is provided a method for biodegrading an aromatic compound or a chlorinated aliphatic hydrocarbon compound by employing a novel strain JMC1 (FERM BP-5960) constitutively expressing oxygenase, which is a mutant strain of JM1 (FERM BP-5352). According to this method, aromatic compounds and chlorinated aliphatic hydrocarbon compounds are efficiently degraded at temperature not higher than 15° C.

According to still another aspect of the invention, there is provided a method for environmental remediation, comprising a step of biodegrading contaminants in the environment by employing a novel strain JMC1 (FERM BP-5960) constitutively expressing oxygenase, which is a mutant strain of JM1 (FERM BP-5352). This method can effectively remedy the environment containing aromatic compounds and chlorinated aliphatic hydrocarbon compounds at temperature not higher than 15° C.

In a series of experiments, the inventors of the present invention isolated a mutant strain JMC1 from the parent strain JM1 (FERM BP-5352) which constitutively expresses oxygenase by placing the parent strain in a cool environment of 4° C. in the initial growth phase. They found that this mutant strain JM1 expresses oxygenase constitutively, thus can degrade aromatic compounds and chlorinated aliphatic hydrocarbon compounds without the presence of an inducer in an environment of low temperature. Hence the inventors have found a method for degrading aromatic compounds and chlorinated aliphatic hydrocarbon compounds, or a method for remedying environment polluted by these chemicals, using this mutant strain JMC1.

DETAILED DESCRIPTION OF THE PREFERRED EMBODIMENTS

Figure 1:
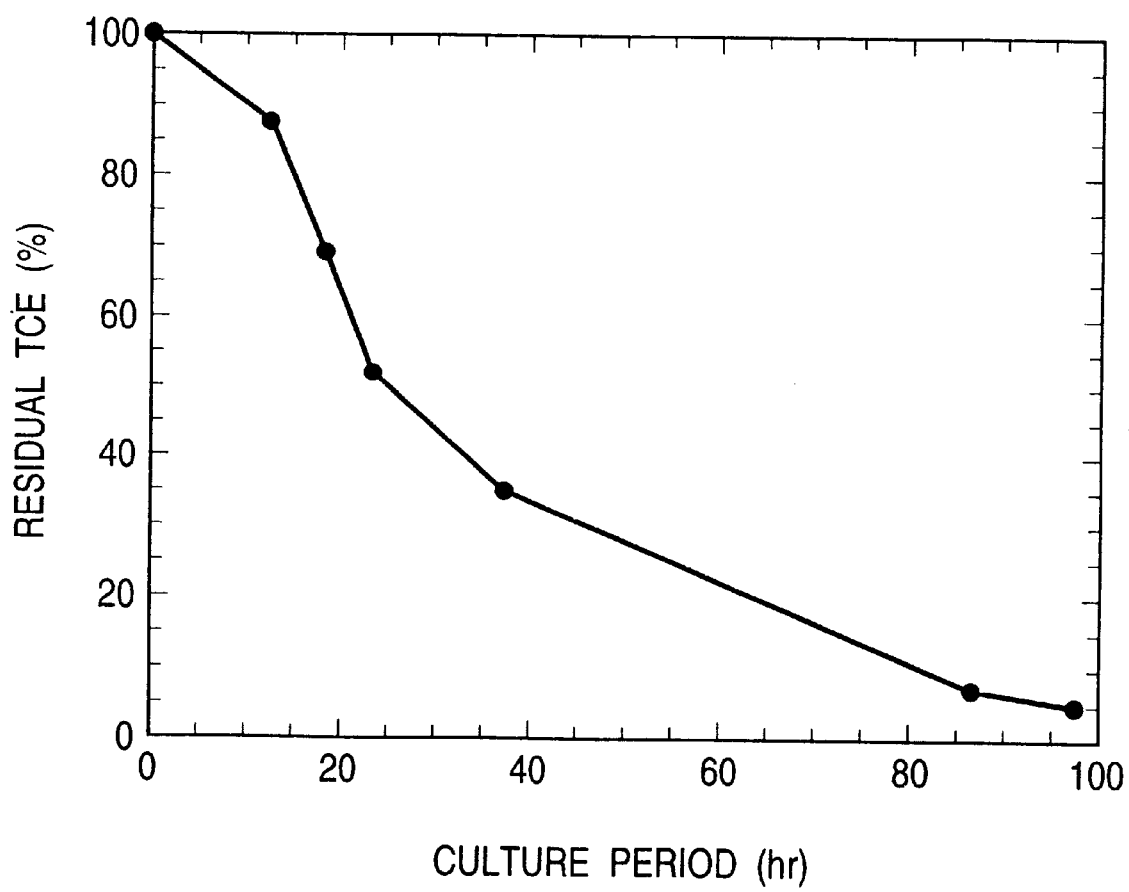
FIG. 1 is a graph showing the degradation of TCE by strain JMC1.

Firstly, microbiological characteristics of strain JM1 (FERM BP-5352) from which the mutant strain according to the invention is derived are listed below.

Gram staining and morphology: Gram negative, rods growth in different culture media:
  BHIA:. good
  MacConkey: possible
Color of the colony: creamy color
Optimum temperature: 25° C.>30° C.>35° C.
Mobility: negative (in a semi-solid culture medium)
TSI (slant/butt): alkaline/alkaline, $H_2S$ (-)
Oxidase: positive (weak)
Catalase: positive
Sugar fermentation:
  glucose: negative
  sucrose: negative
  raffinose: negative
  galactose: negative
  maltose: negative
Urease: positive
Esculin hydrolysis (β-glucosidase): positive
Nitrate reduction: negative
Indole production: negative
Glucose acidification: negative
Arginine dihydrolase: negative
Hydrolysis of gelatin (protease): negative
β-galactosidase: negative
Assimilation of compounds
  glucose: negative
  L-arabinose: negative
  D-mannose: negative
  D-mannitol: negative
  N-acetyl-D-glucosamine: negative
  maltose: negative
  potassium gluconate: negative
  n-capric acid: positive
  adipic acid: negative
  dl-malic acid: positive
  sodium citrate: positive
  phenylacetate: negative Strain JM1 (FERM BP-5352) can assimilate aromatic compounds and degrade chlorinated aliphatic hydrocarbon compounds. Oxygenase participates the process of degradation. It can completely degrade TCE and other chlorinated aliphatic hydrocarbon compounds of a concentration of about 20 ppm at 15° C., a temperature near the soil temperature of in the natural environment.

The mutant strain according to the invention has the same microbiological characteristics as the parent strain JM1 and, additionally, has a potential of growing and biodegrading TCE at a temperature as low as 4° C., where the parent strain JM1 (FERM BP-5352) is practically impotent. This potential is stably maintained after a number of passage cultures so that the inventors of the present invention determined it as a new established microbial strain, named it as JMC1 and deposited it in National Institute of Bioscience and Human-Technology, Agency of Industrial Science and Technology, one of the international depository institutes conforming to the provisions of the Budapest Treaty, on Jul. 13, 1996 (Deposit No. FERM BP-5960).

Strain JMC1 (FERM BP-5960) according to the invention is completely different from $PR1_{301}$ described earlier, since the description on $PR1_{301}$ in Environmental Science & Technology VOL. 30, No. 6, 1986, pp.2045–2052 does not refer to the microbiological characteristics of $PR1_{301}$, it states that $PR1_{301}$ is a spontaneous revertant of *Burkholderia cepacia* $G4_{301}$ derived from *Burkholderia* (*Pseudomonas*) *cepacia* G4 by mutagenizing with N-methyl-N'-nitro-N-nitrosoguanidine (NTG). Therefore, it is considered that $R1_{301}$ has the same microbiological characteristics as the parent strain G4. According to W090/06901, G4 has following microbiological characteristics:
Gram staining and morphology: Gram negative, rods
Urease: negative
Esculin hydrolysis (β-glucosidase): negative
Nitrate reduction: positive
Indole production: negative
Glucose acidification: negative
Arginine dihydrolase: negative
Hydrolysis of gelatin (protease): negative
β-galactosidase: negative
assimilation of each compound
  L-arabinose: positive
  D-mannose: positive
  D-mannitol: positive
  N-acetyl-D-glucosamine: positive
  maltose: negative
  potassium gluconate: positive
  n-capric acid: positive
  adipic acid: negative
  dl-malic acid: positive
  sodium citrate: positive and negative
  phenylacetate: positive The above listed microbiological characteristics of the G4 strain are clearly different from those of strain JMC1 and, therefore, $R1_{301}$ is a microbial strain different from strain JMC1.

Strain JMC1 can degrade aromatic compounds including phenol and cresol as well as chlorinated aliphatic hydrocarbon compounds and hence resistant to these compounds. These compounds are harmful to many microorganisms and many of them are commonly used as microbicides, and often contained in waste liquids in a considerable concentration. If any of such compounds are present, strain JMC1 would survive and its degrading activity would not be inhibited so that chlorinated aliphatic hydrocarbon compounds are efficiently degraded.

Strain JMC1 is highly advantageous in that it does not need the use of an inducer such as phenol for degrading chlorinated aliphatic hydrocarbon compounds contained in underground water and soil. Only ordinary nutrients have to be supplied to the cells to support their growth and biodegradation so that the degradation operation using this strain is simple and free from discharging toxic and harmful inducers into the environment. With a microorganism of which oxygenase is induced by an inducer such as phenol, both chlorinated aliphatic hydrocarbon compounds and the inducer are degraded by the microorganism, resulting in the reduction of the efficiency in the chlorinated aliphatic hydrocarbon compounds degradation by competitive inhibition. On the other hand, strain JMC1 constitutively expresses an oxygenase that is an enzyme for degrading chlorinated aliphatic hydrocarbon compounds, which frees it from competitive inhibition and enables effective and efficient degradation of chlorinated aliphatic hydrocarbon compounds.

Nutritional sources that may be used for growing strain JMC1 of the invention include any ordinary carbon sources, nitrogen sources, or inorganic salt sources used for common microbial culture, if assimilable for this strain. A culture medium such as bouillon medium, M9 medium, 2×YT medium and L broth supplemented with some polypeptone and/or yeast extract can suitably be used for the purpose of the invention.

The composition of M9 medium is shown below.

$Na_2HPO_4$: 6.2 g $KH_2PO_4$: 3.0 g

NaCl: 0.5 g $NH_4Cl$: 1.0 g (per 1 liter, pH 7.0)

Nutrients that can be added to an M9 culture medium for the purpose of the invention include organic acids such as malic acid, citric acid, pyruvic acid, lactic acid, succinic acid and fumaric acid and salts thereof; sugars such as lactose, rhamnose and inositol; and amino acids such as glycine, valine and histidine.

Preferably as inorganic salts, major essential elements for living organisms such as carbon (C), hydrogen (H), nitrogen (N), phosphor (P), potassium (K), calcium (Ca), magnesium (Mg) and sulfur (S) are added to the culture medium in an order of $10^{-2}$ of the dry weight of microorganism, whereas minor essential elements such as iron (Fe), manganese (Mn), copper (Cu), zinc (Zn), chlorine (Cl), boron (B) and molybdenum (Mo) are added in an order of $10^{-5}$ of the dry weight of the microorganism.

The culture can be conducted in an aerobic environment and may be liquid or solid culture. A wide range of culture temperature between 4° C. and 30° C. may be used for the purpose of the invention, although preferably a temperature range between 4° C. and 25° C. is used and more preferably a temperature range between 4° C. and 15° C.

Biodegradation of aromatic compounds and/or chlorinated aliphatic hydrocarbon compounds can be carried out by bringing the aromatic compounds and/or the chlorinated aliphatic hydrocarbon compounds contained in an aqueous medium, soil or in a gaseous phase into contact with strain JMC1 of the present invention. Any method for contacting the microorganisms with the organic compounds can be used, provided the organism can exhibit their decomposition activities, a batch method, semi-continuous method or continuous method being applicable. The microorganisms may be used in semi-immobilized state or may be immobilized on an appropriate carrier. The objects to be treated such as waste liquid, soil or air can be subjected to some pretreatment, if necessary.

The aromatic compounds and/or the chlorinated aliphatic hydrocarbon compounds contained in an aqueous medium as contaminants can be biodegraded by bringing the aromatic compounds and/or the chlorinated aliphatic hydrocarbon compounds into contact with the cells of strain JMC1. For the purpose of the invention, strain JMC1 may be used alone or in combination with another strain. While possible modes of carrying out the present invention are described below, it should be noted that the present invention is by no means limited thereto.

In a most simple mode of carrying out the invention, cells of strain JMC1 are introduced directly into an aqueous medium that is contaminated by aromatic compounds and/or chlorinated aliphatic hydrocarbon compounds. Although it is preferable to adjust pH, salt concentration, temperature and concentration of pollutants in the aqueous medium, strain JMC1 can maintain its decomposition activity unless the environment is under extremely acidic or alkaline conditions or high salt concentration. Additionally, the strain can proliferate and maintain its biodegradation-activeness at temperature as low as 4° C. which is considerably lower than the normal laboratory culture temperature.

In another mode of carrying out the invention, cells of strain JMC1 are cultured in a culture tank, into which an aqueous medium contaminated with aromatic compounds and/or chlorinated aliphatic hydrocarbon compounds is fed at a given rate for biodegradation. The contaminated aqueous medium may be fed and drained continuously, it may alternatively be treated intermittently or in a batch mode depending on the processing capacity of the culture tank. What is important here is to optimize the treatment system depending on the concentration of the contaminants.

In still another mode of carrying out the invention, cells of strain JMC1 are attached to a carrier, for example soil particles, followed by filling the carrier in a reaction vessel, into which an aqueous medium polluted with organic compounds is introduced for decomposition treatment. For this purpose, any carrier can be used as a carrier as well as the soil particles, but those having a high holding capacity for microorganisms and being not obstructive for aeration are more preferable. For example, those commonly used to provide microorganisms with a habitat space in bio-reactors in the pharmaceutical industry, in the food processing industry and in waste water treatment systems can be used. Specific microorganism carriers include inorganic particulate carriers such as porous glass, ceramic, metal oxides, active carbon, kaolinite, bentonite, zeolite, sepiolite, silica gel, alumina and anthracite, gelled carriers such as starch, agar, chitin, chitosan, polyvinylalcohol, alginic acid, polyacrylamide, carrageenan, agarose and gelatin, ion-exchange cellulose, ion-exchange resin, cellulose derivatives, glutaraldehyde, polyacrylic acid, polyurethane and polyester. In addition, natural cellulose materials such as cotton, jute and paper and lignin materials such as saw dust and bark can also be used for the purpose of the invention.

According to the present invention, decomposition treatment of aromatic compounds and/or chlorinated aliphatic hydrocarbon compounds in soil is carried out by the contact of the aromatic compounds and/or chlorinated aliphatic hydrocarbon compounds present in soil with strain JMC1. Representative application modes are described hereinafter, these strains can be used for purifying aromatic compounds and/or chlorinated aliphatic hydrocarbon compounds in any soil without being limited thereto.

A comparatively simple and preferable method comprises directly introducing strain JMC1 into the soil polluted with aromatic compounds and/or chlorinated aliphatic hydrocarbon compounds. Cells of the JMC1 may be sprayed onto the surface of the soil or introduced through a well dug into the soil if a relatively deep underground layer has to be treated. Cells of the JMC1 can spread effectively if driven by air or water under pressure. While various parameters in the soil have to be regulated, strain JMC1 can advantageously be used in soil because strain JMC1 can proliferates more rapidly in the presence of a carrier material like soil particles. Additionally the strain proliferates and maintains its biodegradation-activeness at temperature as low as 4° C. which is considerably lower than the normal soil temperature of 15° C.

In another mode of carrying out the invention, a reaction vessel is filled with a carrier material, to which JMC1 cells are attached, and then buried in the soil, usually the aquifer, contaminated by aromatic compounds and/or chlorinated aliphatic hydrocarbon compounds for biodegradation. The reaction vessel preferably takes such a configuration as a fence or a sheet of film so that it can cover a wide region in the soil. For the purpose of the invention, any carrier material may be used so long as it is effective for carrying microorganisms and does not inhibit aeration. Microorganism carriers that can be used for the purpose of the invention include those commonly used to provide microorganisms with a habitat space in bio-reactors in the pharmaceutical industry, in the food processing industry and in waste water treatment systems. Specific carrier materials include inorganic particulate carriers such as porous glass, ceramic, metal oxides, active carbon, kaolinite, bentonite, zeolite, sepiolite, silica gel, alumina and anthracite, gelled carriers such as starch, agar, chitin, chitosan, polyvinylalcohol, alginic acid, polyacrylamide, carrageenan, agarose and gelatin, ion-exchange cellulose, ion-exchange resin, cellulose derivatives, glutaraldehyde, polyacrylic acid, polyurethane and polyester. In addition, natural cellulose materials such as cotton, jute and paper and lignin materials such as saw dust and bark can also be used for the purpose of the invention.

According to the present invention, aromatic compounds and/or the chlorinated aliphatic hydrocarbon compounds contained in a gaseous phase as contaminants can be biodegraded by bringing the aromatic compounds and/or the chlorinated aliphatic hydrocarbon compounds into contract with the cells of strain JMC1. Possible modes of carrying out the present invention are described below, but not limited thereto.

For example, in a preferred mode of carrying out the invention, cells of strain JMC1 are cultured in a culture tank, into which a gas contaminated by aromatic compounds and/or chlorinated aliphatic hydrocarbon compounds is fed at a given rate for biodegradation. Although contaminated gas may be fed by any means, the liquid culture is preferably agitated by the introduced gas to promote the aeration of the system. Contaminated gas may be fed and exhausted continuously, intermittently or in a batch mode depending on the processing capacity of the culture tank. What is important here is to optimize the treatment system depending on the concentration of the contaminants.

In another mode of carrying out the invention, cells of strain JMC1 are attached to a carrier, for example soil particles, followed by filling the carrier in a reaction vessel, into which a gaseous medium polluted with organic compounds is introduced for decomposition treatment. For this purpose, any carrier can be used as a carrier as well as the soil particles, but those having a high holding capacity for microorganisms and being not obstructive for aeration are more preferable. For example, those commonly used to provide microorganisms with a habitat space in bio-reactors in the pharmaceutical industry, in the food processing industry and in waste water treatment systems can be used. Specific carrier materials include inorganic particulate carriers such as porous glass, ceramic, metal oxides, active carbon, kaolinite, bentonite, zeolite, sepiolite, silica gel, alumina and anthracite, gelled carriers such as starch, agar, chitin, chitosan, polyvinylalcohol, alginic acid, polyacrylamide, carrageenan, agarose and gelatin, ion-exchange cellulose, ion-exchange resin, cellulose derivatives, glutaraldehyde, polyacrylic acid, polyurethane and polyester. In addition, natural cellulose materials such as cotton, jute and paper and lignin materials such as saw dust and bark can also be used for the purpose of the invention.

Materials that can be used to keep and feed microorganisms for the purpose of the invention include composts and many other similar products popular in agriculture and fishery such as grain straw, saw dust, rice bran, dried lees of bean-curd, bagasse and other dried plant products as well as fishery wastes including crab shells and prawn shells.

To treat contaminated gas for the purpose of the invention, cells may be introduced into a tank filled with a carrier material in advance or they themselves may be cultured in advance. The nutrient supply rate, the water content, the oxygen concentration and other factors should be held to respective preferably levels for effective biodegradation. The ratio between the volume of the carrier and water content in the reaction vessel may be selected considering the microbial growth and aeration efficiency, and the shape of the reaction vessel can be appropriately determined depending on the volume and pollutant concentration of the air to be treated. Care should be taken to ensure the contact between the gas and the cells held by the carrier. For example, it may take the form of a column, a tube, a tank or a box. The reaction vessel may be combined with an exhaust duct and a filter set into a unitized entity or a number of reaction vessels may be arranged in series to realize a desired treatment capacity.

The contaminated gas fed into a reaction vessel may adhere to the carrier firsthand and there may be rare occasions where the effect of utilizing the microorganism is not conspicuously observed particularly in the initial stages of operation, the contaminants on the carrier are decomposed after a certain period of time and new pollutant is adsorbed on the surface of the carrier from which the first pollutant was removed by decomposition so that the capacity of the reaction vessel will not be saturated and the biodegradation process can be held to a constant level.

Any culture media normally used for culturing microorganisms as described above can suitably be used for strain JMC1 in a treatment process using a method according to the invention. More specifically, culture media such as bouillon medium, M9 medium, 2×YT medium, L medium or a medium containing polypeptone, yeast extract and carbon sources such as sugars and organic acids in a proper ratio are effective. These media are effective in a liquid form or a gel form prepared by adding agarose to the liquid form.

A method according to the invention may be used with a closed or open system for treating waste water, soil and/or air. It may be combined with methods for anchoring microorganisms to a carrier and/or promoting the growth of microorganisms.

Now, the present invention will be described in greater detail by way of examples, although these examples do not limit the scope of the present invention by any means.

EXAMPLE 1

Isolation of Strain JMC1 and Oxygenase Analysis

Cells of strain JM1 grown on an agar medium are inoculated into 100 ml of M9 medium containing 1% sodium malate in a Sakaguchi flask, and subjected to a shaking culture at 22° C. for 23 hours. At this point, the cell density of strain JM1 in the Sakaguchi flask reached $4\times10^8$ cells/ml. Then, three 2 ml aliquots of the culture were taken and diluted by consecutive 10-fold dilutions to obtain dilutions of $4\times10^3$ cells/ml, $4\times10^2$ cells/ml and $4\times10$ cells/ml, respectively. Thereafter, from each dilution, 100 μl was taken in duplicate and spread on M9 agar plates containing 1% sodium malate. Total 2×3 agar plates inoculated with JM1 cells were then incubated at 4° C. for six days followed by the incubation at room temperature (22° C.) for 3 days. On one of two agar plate spread with a $10^5$-fold dilution, milky white colonies appeared (hereinafter referred to as "Colony A").

As controls, 100 μl was taken from each of the dilutions in duplicate and spread on M9 agar plates containing 1% sodium malate. These 2×3 plates spread with JM1 cells were incubated at room temperature (22° C.) for 3 days to find that all agar plates were grown with milky white colonies of strain JM1 (hereinafter referred to as "Colony B").

Then, cells of Colony A and Colony B were separately inoculated in 100 ml M9 medium containing 2% sodium malate in a Sakaguchi flask and subjected to a shaking culture at 4° C. for 7 days. As a result, the number of cells from Colony A rose from the initial $3\times10^6$ cells/ml to $1.5\times10^8$ cells/ml after 7 days. On the other hand, the number of cells from Colony B rose from the initial $3\times10^6$ cells/ml to about $5.2\times10^7$ cells/ml.

Meanwhile, cells taken from Colony A and Colony B were separately inoculated in 200 ml M9 medium containing 0.2% yeast extract in a Sakaguchi flask and subjected to a shaking culture at 22° C. for 24 hours. Then each cell pellet collected by centrifugation were crushed by a French press to obtain a cell extract. Catechol-1,2-oxygenase (C12O) and catechol-2,3-oxygenase (C23O) in the cell extract of each Colony A and Colony B were determined by spectroscopy (Microbiol., 6B, 463–478 (1977)). Protein quantity was determined using a Biolad Protein Assay Kit. The result is shown in Table 1.

TABLE 1

| C12O and C23O Activities (μmol/min/mg protein) | | |
|---|---|---|
| | C12O | C23O |
| Colony A | 0.101 | 1.93 |
| Colony B (JM1) | 0.103 | 1.96 |

From above, it was confirmed that the cells of Colony A constitutively express oxygenase as strain JM1.

Comparison of Colony A and strain JM1

Figure 4:
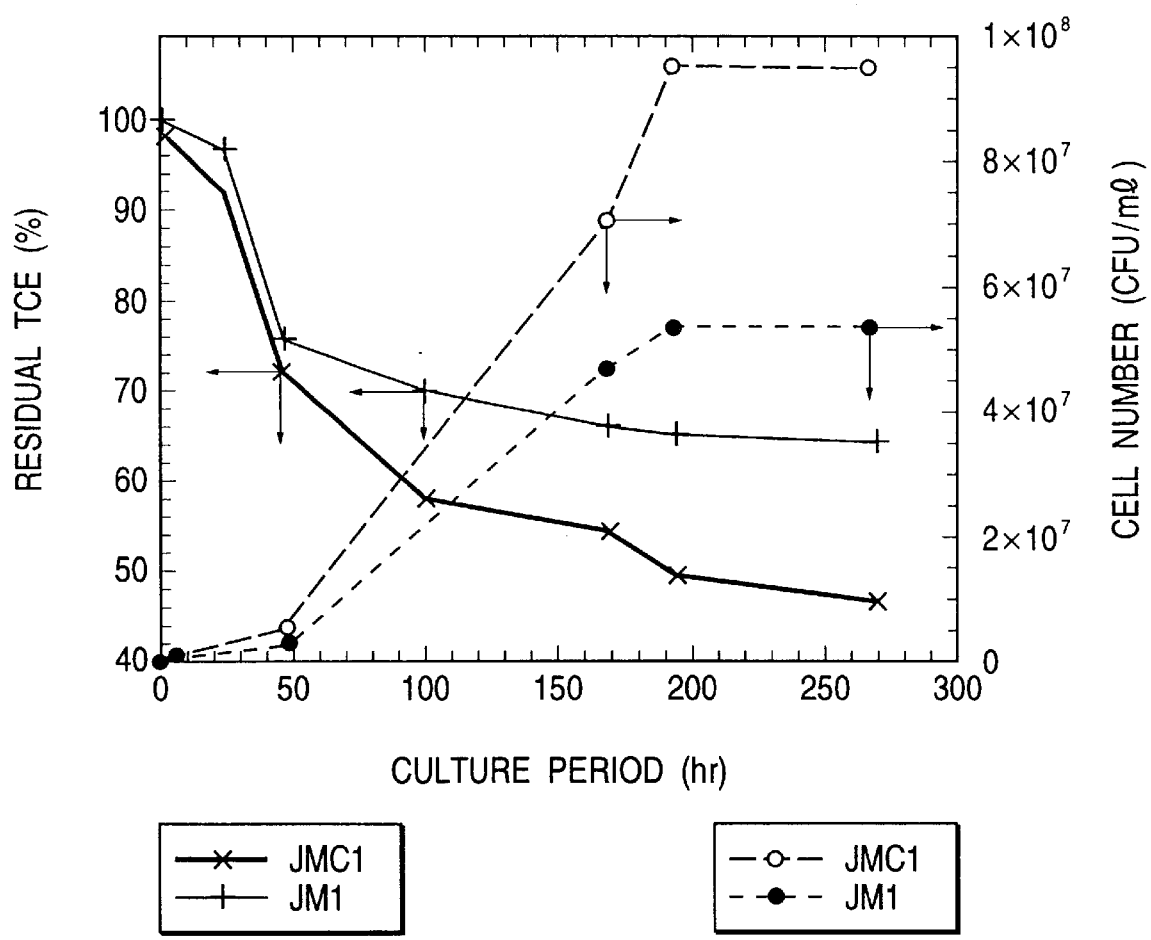
FIG. 4 is a graph to compare strain JM1 with strain JMC1 on growth and TCE degradation.

(1) An experiment was conducted to compare the cells of Colony A which are different from strain JM1 in growth properties at 4° C. with the cells of strain JM1. Colony A cells and JM1 cells were separately inoculated in 100 ml M9 medium (2% sodium malate) in a Sakaguchi flask, and subjected to shaking culture. The cell growth was monitored at regular intervals by plate count for both cultures. FIG. 4 shows the results.

Meanwhile, Colony A cells and JM1 cells were separately inoculated in 200 ml M9 medium containing 2% sodium malate in a Sakaguchi flask, and subjected to shaking culture at 4° C. for 7 days. Then, a plurality of vials were divided into two groups and each vial contained 5 ml of M9 medium containing 20 ppm TCE and 1% sodium malate as a carbon source. To each vial of one group, 0.1 ml of Colony A culture cultured at 4° C. for 7 days as described above was inoculated and 0.1 ml of strain JM1 to each vial of the other group. Thereafter, each vial was hermetically sealed with a butyl rubber stopper and an aluminum cap and cultured with shaking at 4° C. Then, the TCE degradation by microorganisms was monitored at regular intervals by head space gas chromatography. As a control, a similar experiment system containing TCE at the same concentration but no microorganisms was constructed and TCE was quantified at regular intervals. The ratio of the residual TCE to the control TCE was determined. The results are shown in FIG. 4.

As seen from FIG. 4, the cells of Colony A showed far greater potentials for growth and TCE degradation at 4° C. than strain JM1.

(2) Next, a colony of Colony A grown on an agar medium was inoculated in 200 ml M9 medium supplemented with 2% sodium malate in a Sakaguchi flask and cultured with shaking at 4° C. for 7 days. Culture in a Sakaguchi flask was repeated 5 times and the microorganisms obtained from the fifth passage culture were tested for the potential for growth and TCE degradation at 4° C. in the same manner as described above. The results were the same as those shown in FIG. 4 for Colony A. More specifically, although cells of Colony A constitutively expresses oxygenase as strain JM1 and has the same microbiological characteristics as those of strain JM1, the former is far better than the latter at growth and TCE degradation at low temperature (4° C.) and the potential was not reduced by passage culture. Thus, the inventors of the present invention determined that the Colony A cells were of a mutant strain derived from strain JM1 and named the new strain as JMC1, which was then deposited in the National Institute of Bioscience and Human-Technology, Agency of Industrial Science and Technology (FERM BP-5960).

EXAMPLE 2

Degradation of TCE by strain JMC1 (Liquid Culture System at 10° C.)

A colony on an agar medium of strain JMC1 obtained as described in Example 1 was inoculated in 200 ml of M9 medium containing 2% sodium malate in a Sakaguchi flask and subjected to shaking culture at 15° C. for 70 hours.

Meanwhile 5 ml of M9 medium containing TCE by 20 ppm and sodium malate by 1% as carbon source was put into a vial to which 0.1 ml of the above culture inoculated. The vial was hermetically sealed by means of a butyl rubber stopper and an aluminum cap and subjected to shaking culture at 10° C. The TCE degradation with time by the microorganism was monitored at regular intervals by a head space gas chromatography method. As a control, a similar experiment system containing TCE at the same concentration but no JMC1 cells was constructed, and TCE was quantified at regular time intervals. The ratio of residual TCE to the control TCE was determined. The results are summarily shown in FIG. 1. As seen from FIG. 1, it was demonstrated that strain JMC1 can degrade TCE in a liquid culture system at 10° C.

EXAMPLE 3
Degradation of DCE by strain JMC1 (Liquid Culture System at 15° C.)

Figure 2:
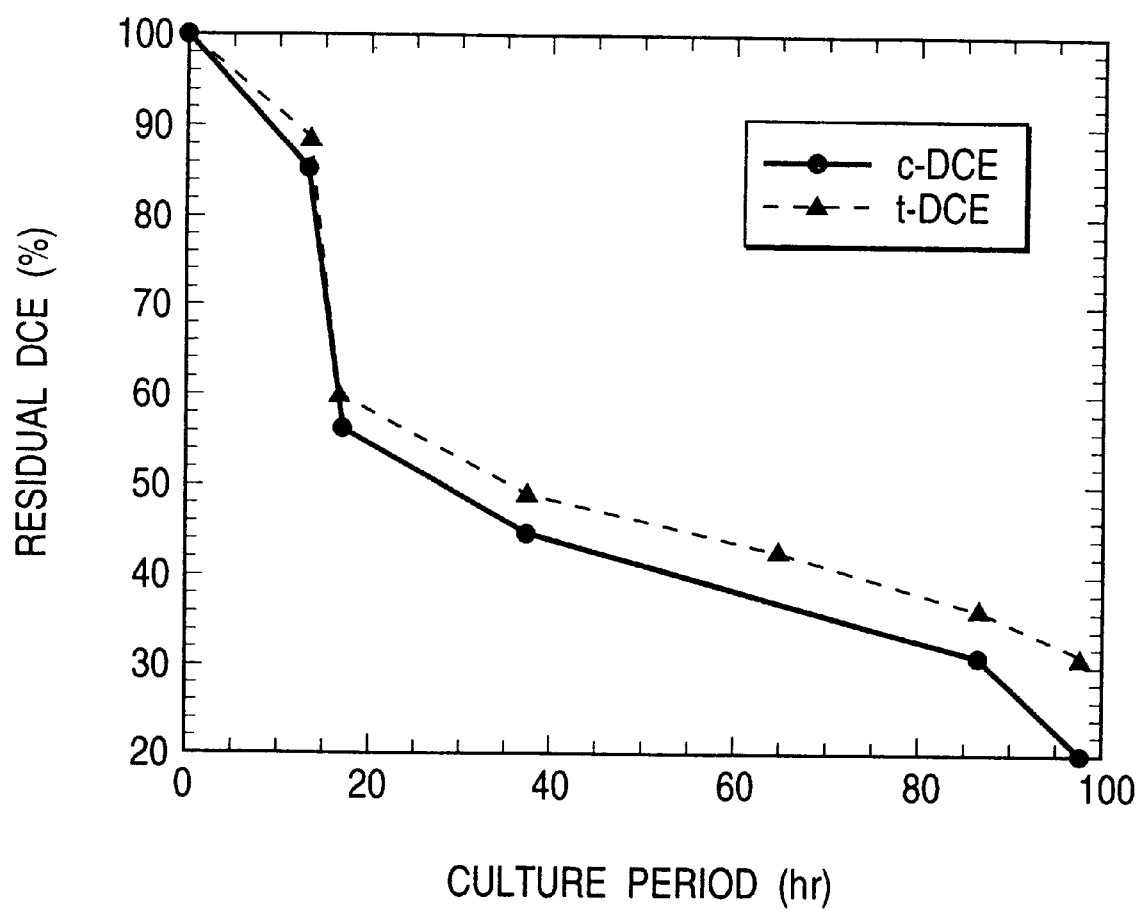
FIG. 2 is a graph showing the degradation of DCE by strain JMC1.

The procedures of Example 1 were followed except that the compound to be degraded was changed to cis-1,2-dichloroethylene (cis-1,2-DCE) (8 pm) and trans-1,2-dichloroethylene (trans-1,2-DCE) (8 ppm) and the temperature was raised to 15° C. to see the reduction of DCE with time. FIG. 2 shows the results (where c-DCE and t-DCE refer respectively to cis-1,2-DCE and trans-1,2-DCE). As seen from FIG. 2, it was demonstrated that strain JMC1 can degrade DCE in a liquid culture system at 15° C.

EXAMPLE 4
Degradation of Aromatic Compounds by strain JMC1 (Liquid Culture System at 15° C.)

Figure 3:
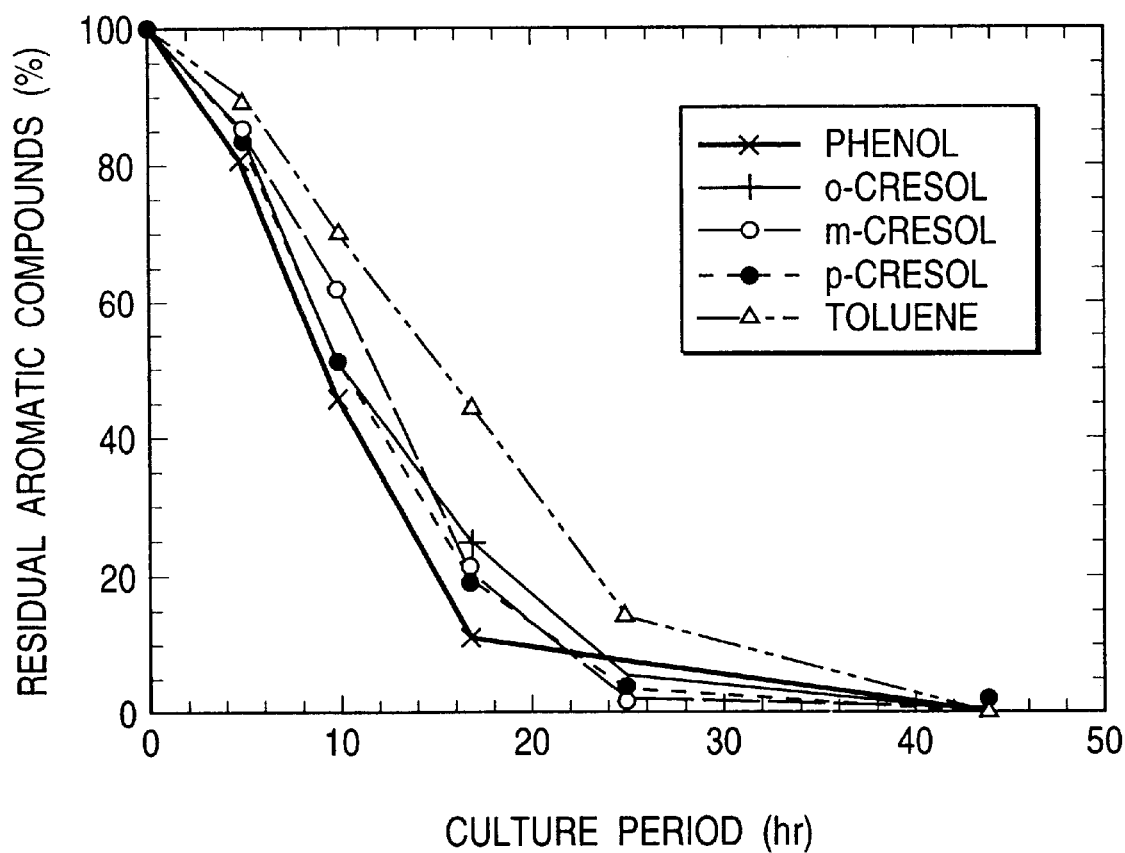
FIG. 3 is a graph showing the degradation of aromatic compounds by strain JMC1.

The procedures of Example 1 were followed except that the carbon source of M9 medium was changed to 0.1% yeast extract and TCE was replaced by phenol, o-cresol, m-cresol, p-cresol and toluene respectively at a concentration of 10 ppm, to determine the reduction of the aromatic compounds with time. Liquid chromatography was used for phenol and cresol, whereas gas chromatography was used for toluene. FIG. 3 shows the results. As seen from FIG. 3, it was demonstrated that strain JMC1 can degrade the above aromatic compounds in a liquid culture system at 15° C.

EXAMPLE 5
Degradation of TCE in Soil by strain JMC1 (Sawara sieved Sand at 10° C.)

Figure 5:
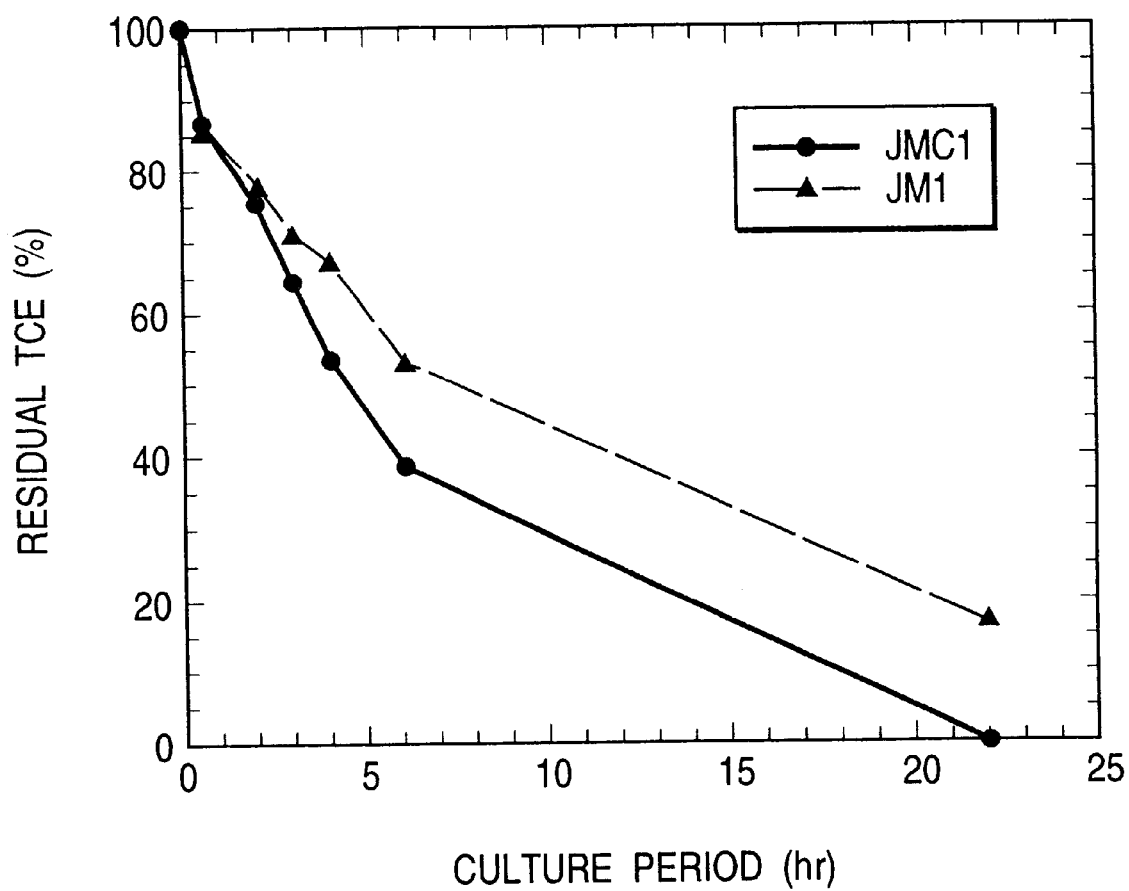
FIG. 5 is a graph showing the degradation of TCE in soil by strain JM1 and strain JMC1.

A plurality of 68 ml vials were prepared and to each vial, 3 ml of M9 medium containing 50 ppm TCE and 2% sodium citrate and 30 g of Sawara sand (sterilized by autoclaving at 120° C. for 10 minutes) were put. While, a colony of strain JMC1 grown on an agar medium was inoculated in 200 ml of M9 medium containing sodium malate by 2% in a Sakaguchi flask and subjected to shaking culture at 4° C. for 7 days. Then, 0.3 ml of this culture was inoculated into each of the vials and the vials were hermetically sealed by means of a butyl rubber stopper and an aluminum cap and left statically at 10° C. Then, the TCE degrading performance of the strain of microorganism was observed at regular time intervals by a head space gas chromatography method. As a control, a similar experiment system containing TCE at the same concentration but no JMC1 cells was constructed to determine TCE at regular time intervals. The ratio of the residual TCE to the control TCE was determined. The results are shown in FIG. 5.

EXAMPLE 6
Degradation of TCE in Soil by strain JMC1 (Sawara sieved Sand at 4° C.)

Figure 6:
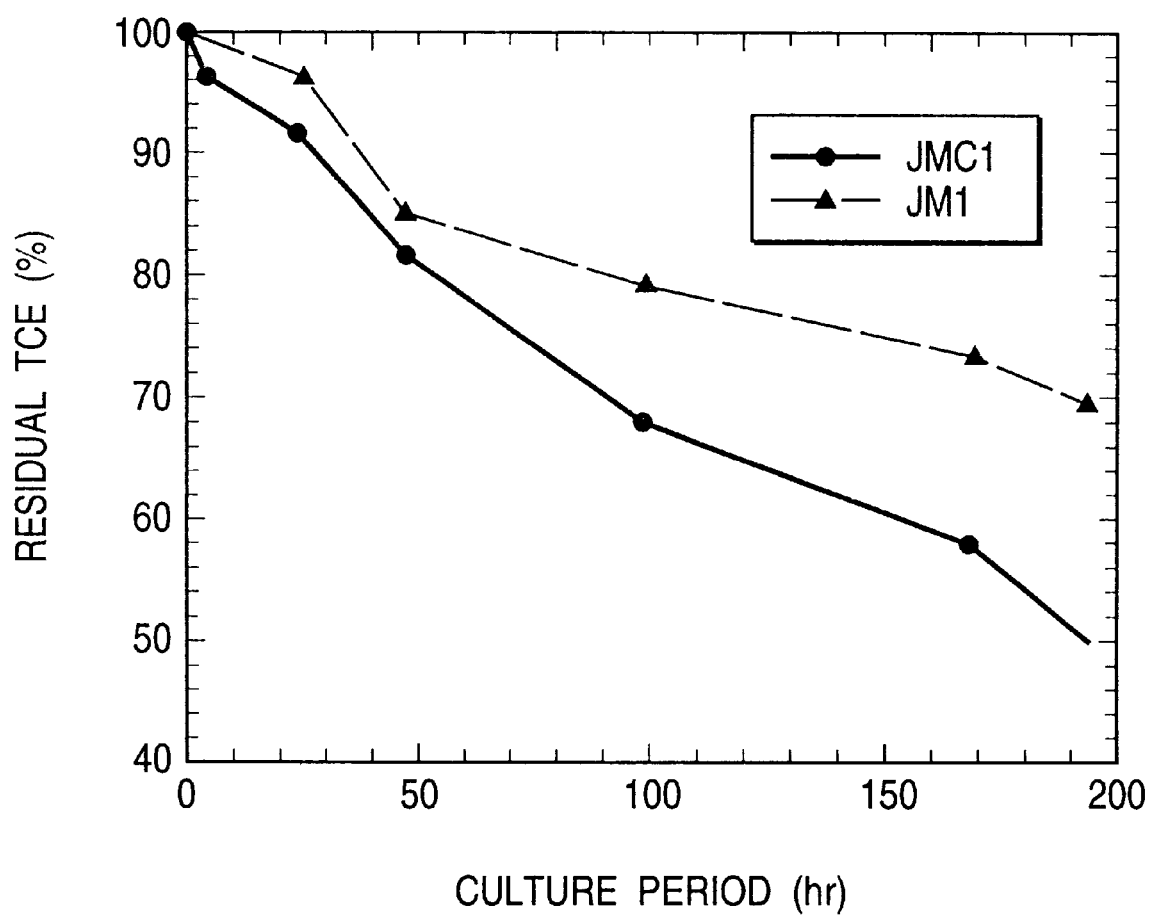
FIG. 6 is a graph also showing the degradation of TCE in soil by strain JM1 and strain JMC1.

The procedures of Example 5 were followed except that the soil temperature was held at 4° C., to determine TCE degradation with time. The results are shown in FIG. 6. As seen from FIG. 6, it was demonstrated that strain JMC1 can degrade TCE in soil at 4° C.

EXAMPLE 7
Degradation of TCE in Soil by strain JMC1 (Kanto Loam at 8° C.)

Figure 7:
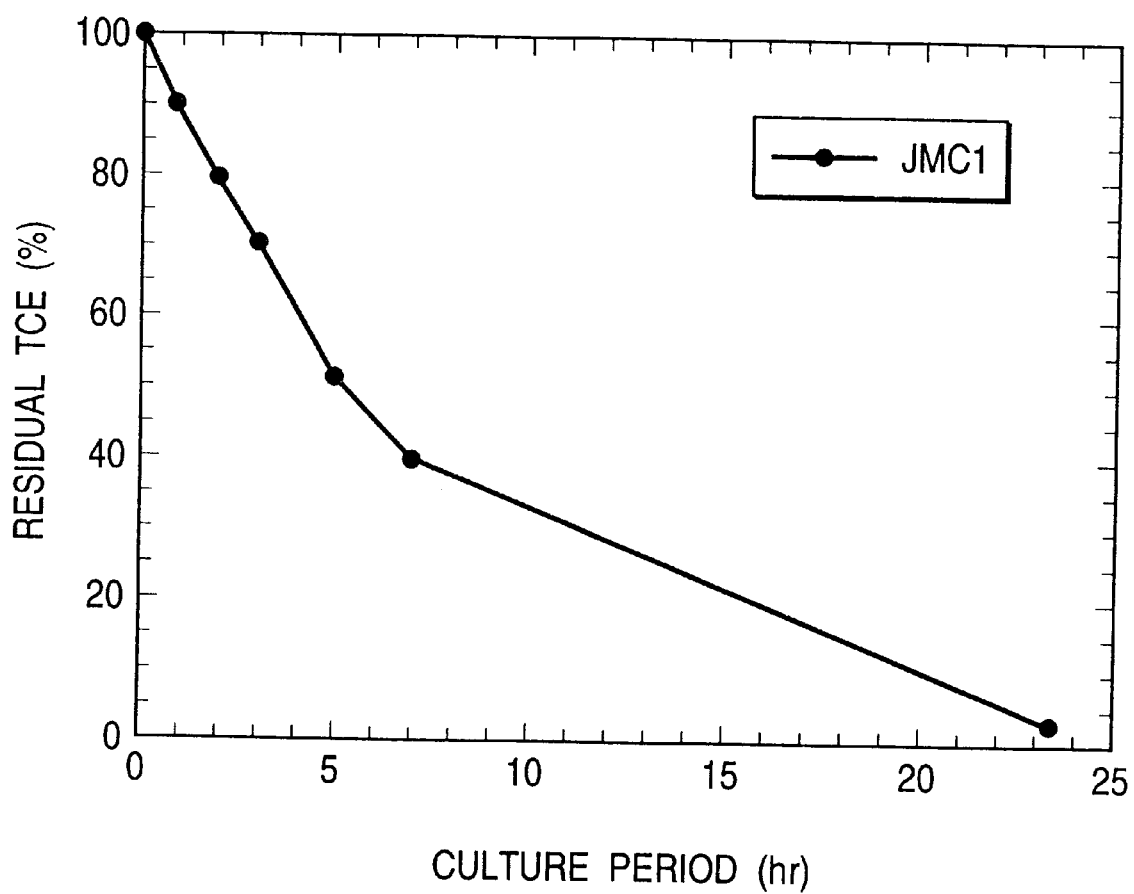
FIG. 7 is a graph showing the degradation of TCE in soil by strain JMC1.

The procedures of Example 5 were followed except that the soil was changed from sand to loam and the temperature was held at 8° C., to determine the TCE decrease with time. The results are shown in FIG. 7. As seen from FIG. 7, it was demonstrated that strain JMC1 can degrade TCE in soil at 8° C.

EXAMPLE 8
Degradation of DCE in Soil by strain JMC1 (Brown Forest Soil at 8° C.)

The procedures of Example 6 were followed except that the following four items were changed to determine the decrease of the object compound with time;
1. Chemical to be degraded: cis-1,2-dichloroethylene (cis-1,2-DCE), trans-1,2-dichloroethylene (trans-1,2-DCE) or 1,1-dichloroethylene (1,1-DCE) instead of TCE,
2. Concentration: 10 ppm instead of 50 ppm,
3. Nutrient: Sodium malate instead of sodium citrate,
4. Degradation Temperature: 8° C. instead of 5° C.

Figure 8:
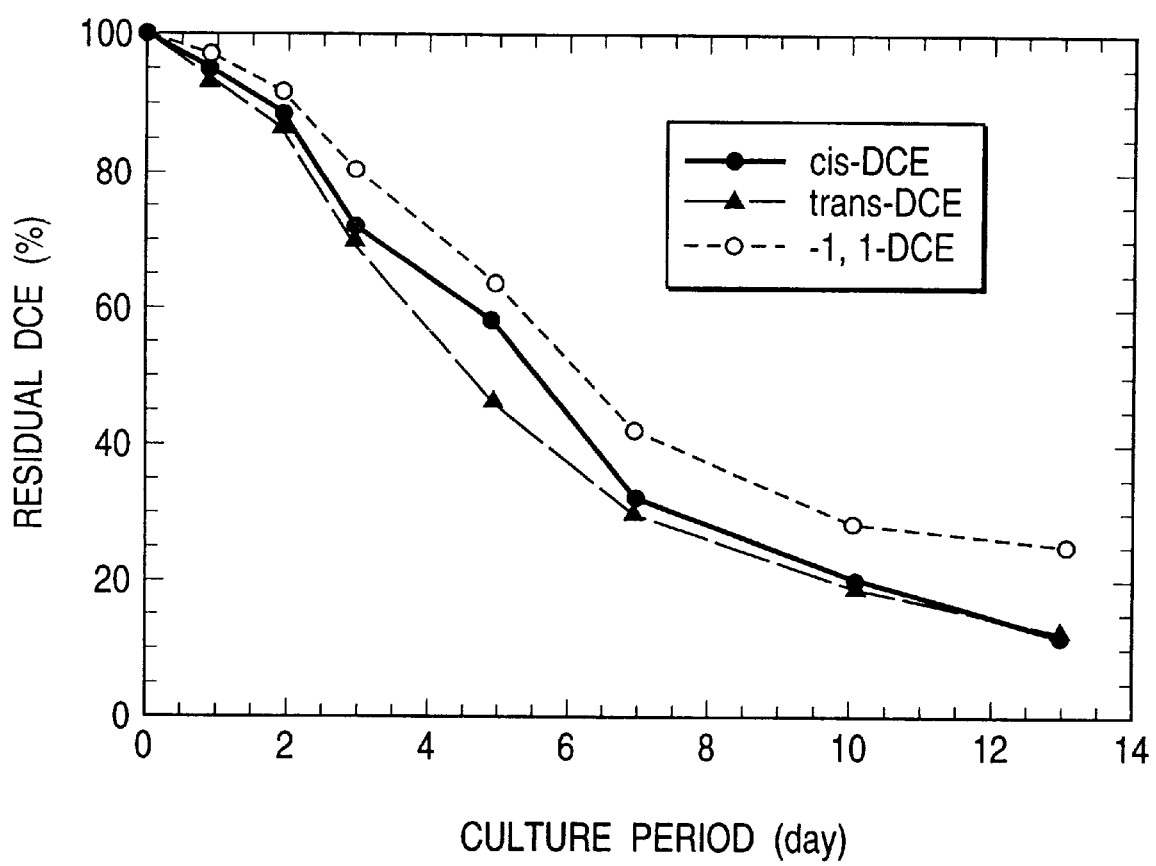
FIG. 8 is a graph showing the degradation of DCE in soil by strain JMC1.

FIG. 8 shows the results.

EXAMPLE 9
Degradation of Phenol in Soil by Strain JMC1 (Brown Forest Soil at 10° C.)

Figure 9:
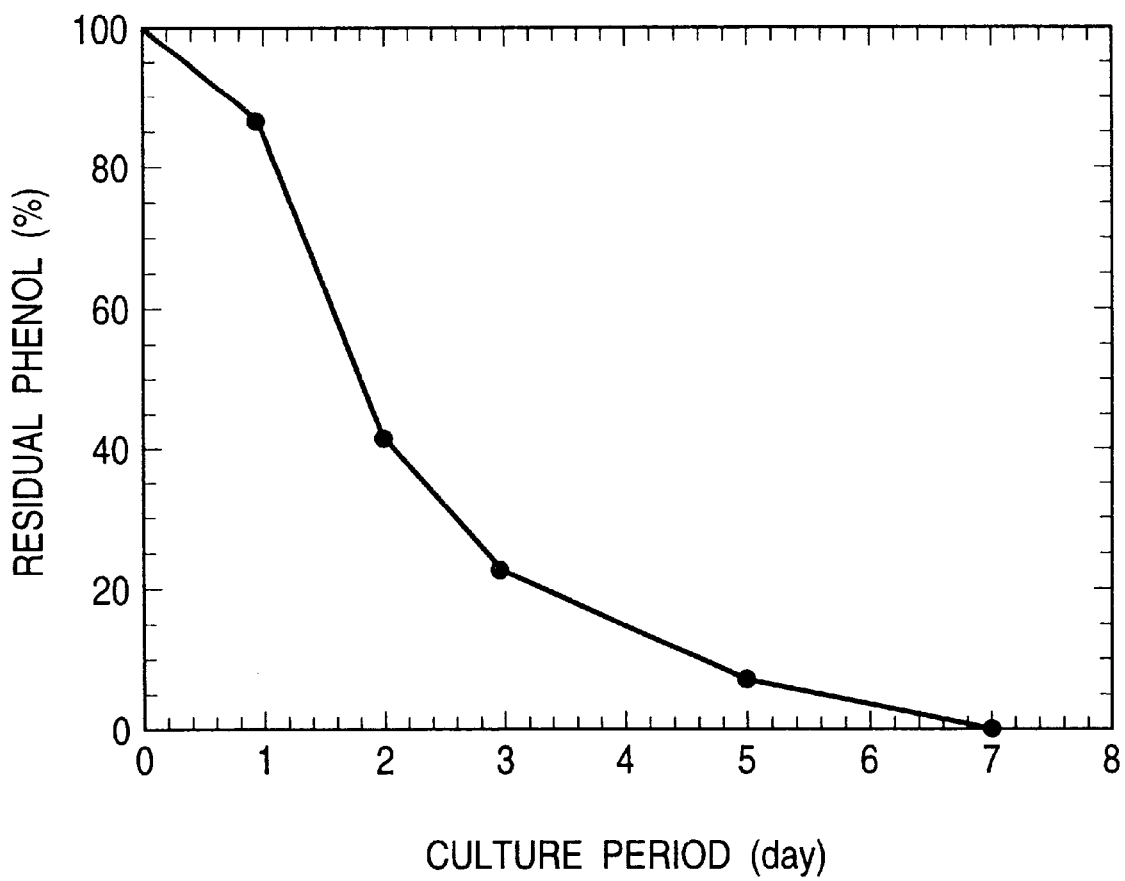
FIG. 9 is a graph showing the degradation of phenol in soil by strain JMC1.

The procedures of Example 8 were followed except that the compound to be degraded was 100 ppm phenol, of which decrease was determined with time. Phenol was quantified by JIS method (JIS K 0102-1993, 28. 1) using aminoantipyrine. The results are shown in FIG. 9. As seen from FIG. 9, it was demonstrated that strain JMC1 can degrade phenol in soil at 10° C.

Figure 10:
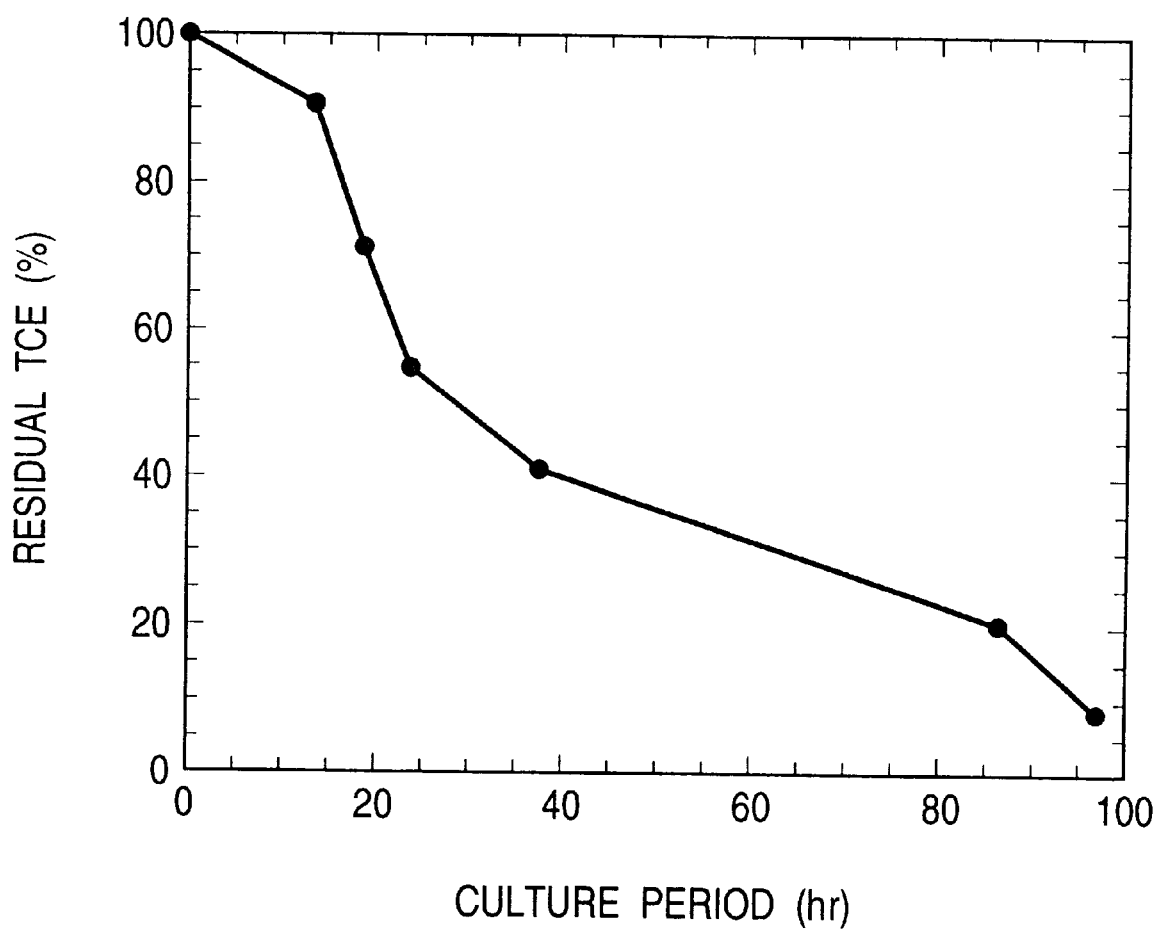
FIG. 10 is a graph showing the degradation of TCE in a gaseous phase by strain JMC1.

EXAMPLE 10
Degradation of TCE in a Gaseous Phase by Exposing to JMC1 Liquid Culture As in Example 1, a colony of strain JMC1 grown on an agar medium was inoculated in 100 ml M9 medium containing 2% sodium malate in a Sakaguchi flask and subjected to shaking culture at 4° C. for 7 days. Then, 0.1 ml of the above culture was added to a vial containing 30 ml of M9 medium supplemented with 0.5% sodium citrate. Air which had aerated a saturated TCE solution was flowed through the liquid in the vial at a rate of 60 ml/min for 30 minutes, and then the vial was hermetically sealed by means of a butyl rubber stopper and an aluminum cap and subjected to shaking culture at 10° C. The TCE quantity was determined with time by a head space gas chromatography method. As a control, a similar experiment system containing TCE at the same concentration but no JMC1 cells was constructed and the TCE was quantified concomitantly. The ratio of the residual TCE to the control TCE was determined. The results are shown in FIG. 10. As seen from FIG. 10, it was demonstrated that strain JMC1 can degrade TCE in a gaseous phase at 10° C.

Figure 11:
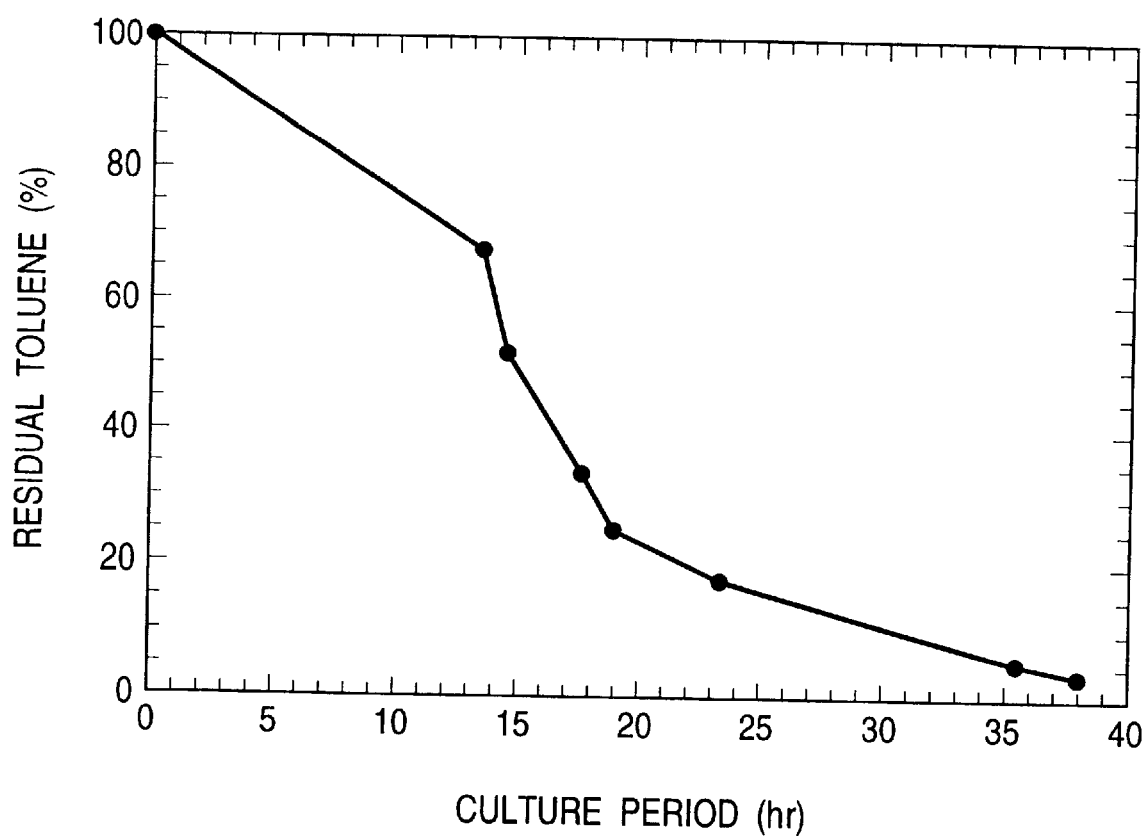
FIG. 11 is a graph showing the degradation of toluene in a gaseous phase by strain JMC1.

EXAMPLE 11
Degradation of Toluene in a Gaseous Phase by Exposing to a Liquid JMC1 Culture The procedures of Example 10 were followed except that TCE was replaced by toluene, to determine the decrease of toluene with time. Toluene was quantified by a head space gas chromatography method with time. The results are summarily shown in FIG. 11. As seen from FIG. 10, it was demonstrated that strain JMC1 can degrade toluene in a gaseous phase at 10° C.

EXAMPLE 12
Degradation of DCE in a Gaseous Phase by Aerating Soil Containing strain JMC1

Figure 12:
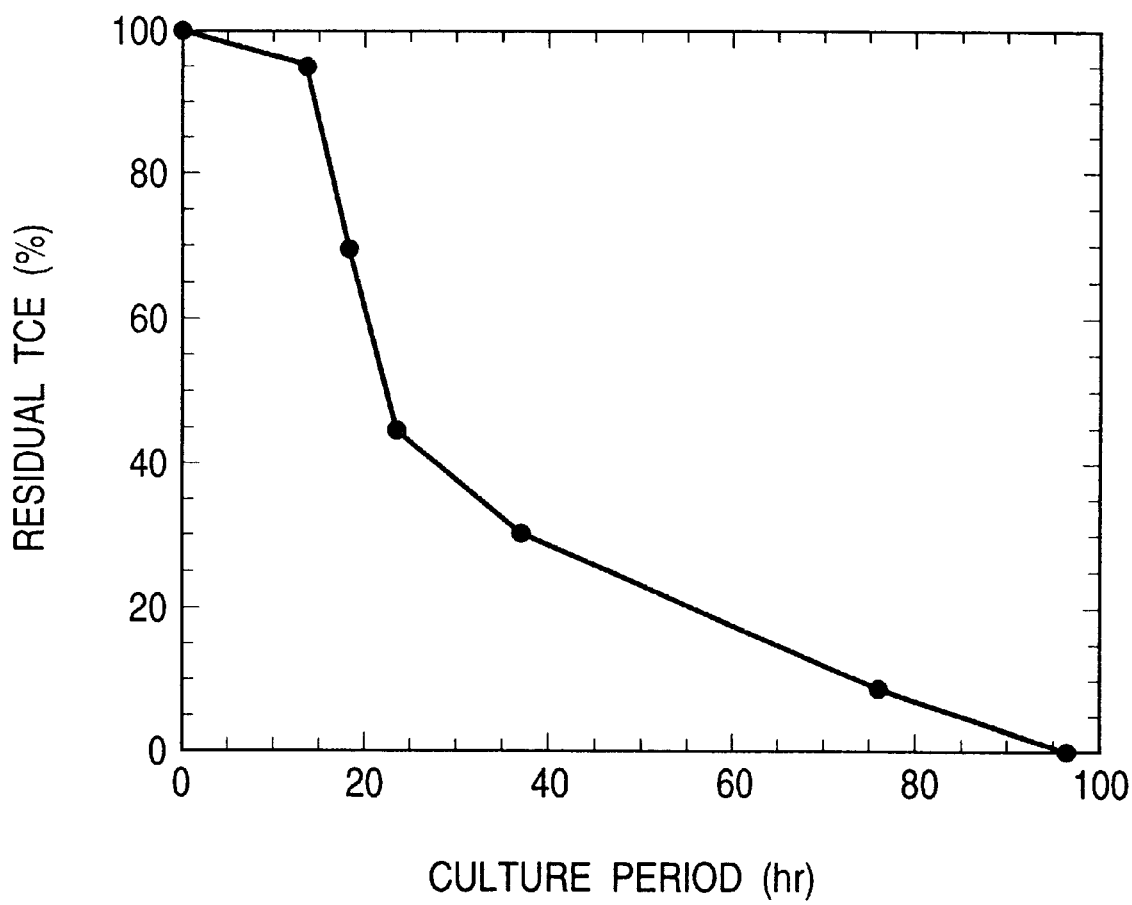
FIG. 12 is a graph showing the degradation of TCE in a gaseous phase by aeration of a soil containing strain JMC1.

A culture of strain JMC1 was prepared in the same manner as in Example 10, and 0.1 ml of the culture was added to 30 ml of M9 medium containing 2% sodium malate in a vial, to which sterilized brown forest soil was added until it reached to the surface of the liquid. The vial was hermetically sealed by means of a butyl rubber stopper and left statically overnight at 13° C. and thereafter superfluous liquid was discarded by decantation. Then, air which had aerated a saturated TCE solution was flowed through the soil in the vial at a rate of 65 ml/min for 30 minutes. Then the vial was hermetically sealed by means of a butyl rubber stopper and an aluminum cap and subjected to static culture at 13° C. The TCE concentration was quantitatively determined by a head space gas chromatography method with time. FIG. 12 shows the results.

EXAMPLE 13

Degradation of DCE in a Gaseous Phase by Continuous Aeration of Liquid Culture of JMC1

Figure 13:
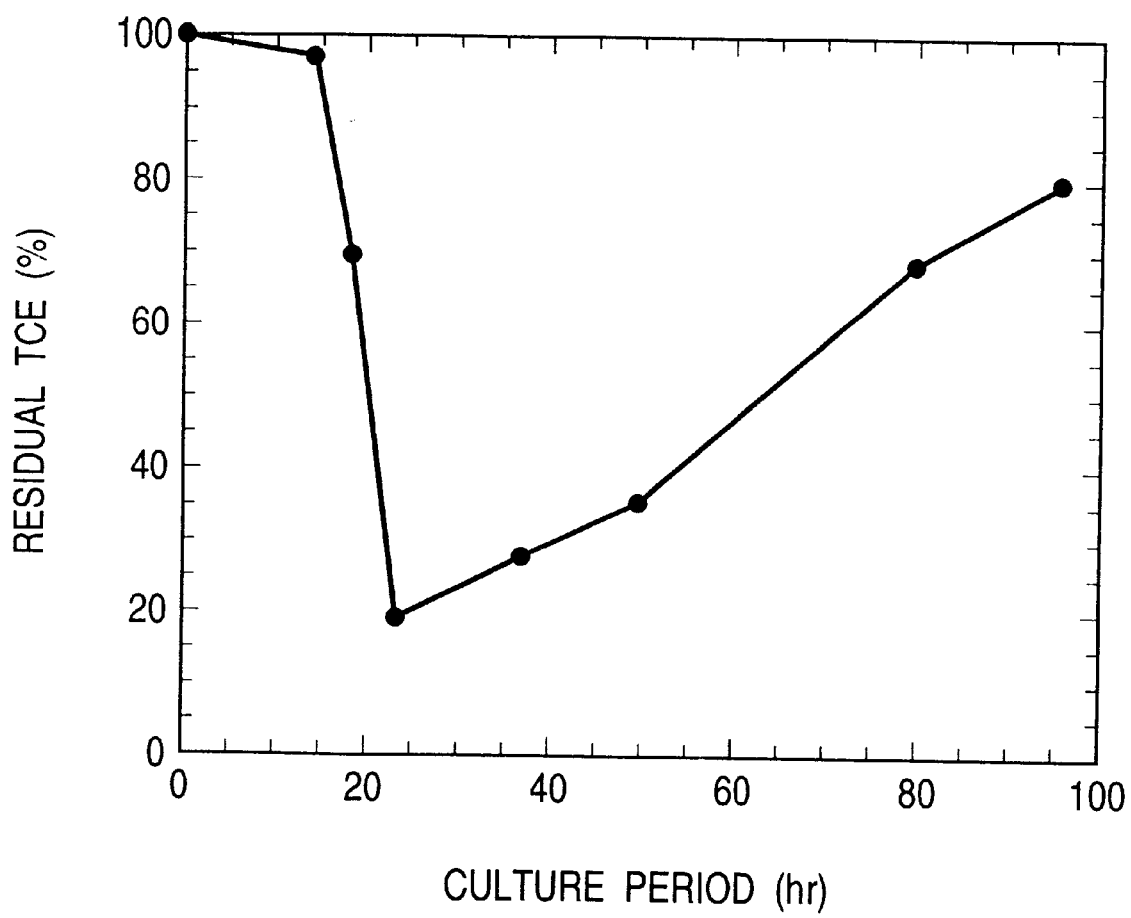
FIG. 13 is a graph showing the degradation of TCE in a gaseous phase by continuous aeration of the liquid culture of strain JMC1.

A culture of strain JMC1 was prepared in the same manner as in Example 10, and 0.1 ml of the culture was added to 30 ml of M9 medium containing 2% sodium malate in a vial. The vial was hermetically sealed by means of a butyl rubber stopper. Thereafter, air which had aerated a saturated TCE solution was continuously flowed into the liquid culture in the vial at a rate of 0.5 ml/min, under static culture at 10° C. The TCE in the exhaust air was determined with time by gas chromatography. FIG. 13 shows the results.

EXAMPLE 14

Degradation of DCE in a Gaseous Phase by Continuous Aeration of Soil Containing strain JMC1

Figure 14:
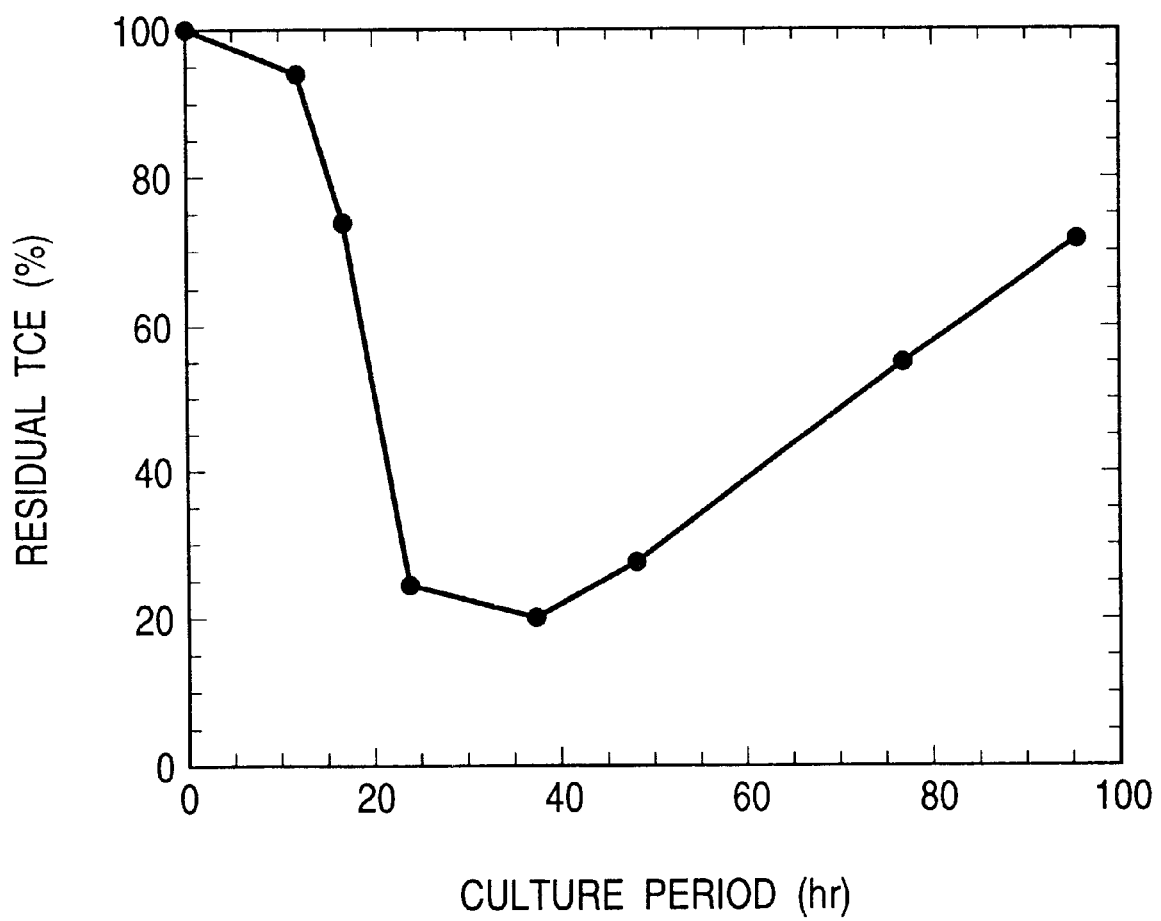
FIG. 14 is a graph showing the degradation of TCE in a gaseous phase by continuous aeration of soil containing strain JMC1.

A culture of strain JMC1 was prepared in the same manner as in Example 10, and 0.1 ml of the culture was added to 30 ml of M9 medium containing 0.1% yeast extract in a vial, to which sterilized brown forest soil was added until it reached to the surface of the liquid. The vial was hermetically sealed by means of a butyl rubber stopper and left statically overnight at 13° C. and thereafter superfluous liquid was discarded by decantation. After the vial was hermetically sealed by means of a butyl rubber stopper and an aluminum cap, air which had aerated a saturated TCE solution was continuously flowed through the soil in the vial at a rate of 0.5 ml/min under static culture at 30° C. The TCE in the exhaust air was determined with time by gas chromatography. FIG. 14 shows the results.

As seen from the above examples, the novel JMC1 strain can effectively degrades aromatic compounds and/or chlorinated aliphatic hydrocarbon compounds contained in an aqueous medium, soil or in a gaseous phase at temperature not higher than 15° C.

What is claimed is:

1. A bacterial strain JMC1 (FERM BP-5960), the strain JMC1 being a mutant strain derived from JM1 (FERM BP-5352) constitutively expressing oxygenase, wherein the strain JMC1 has an ability to proliferate and on and degrade an aromatic compound and a chlorinated aliphatic hydrocarbon compound constitutively at 4° C.

2. A method of biodegrading an aromatic compound or a chlorinated aliphatic hydrocarbon compound at a temperature between 4° C. and 15° C., comprising the steps of:
  (a) contacting a bacterial strain JMC1 (FERM BP-5960) with the aromatic compound or the chlorinated aliphatic hydrocarbon compound, wherein the strain JMC1 is a mutant strain derived from strain JM1 (FERM BP-5352) constitutively expressing oxygenase and the strain JMC1 has an ability to proliferate on and degrade the aromatic compound and the chlorinated aliphatic hydrocarbon compound consitutively at 4° C.; and thereby
  (b) degrading the aromatic compound or the chlorinated aliphatic hydrocarbon compound with the strain JMC1 (FERM BP-5960).

3. The method according to claim 2, wherein the aromatic compound is at least one compound selected from the group consisting of phenol, toluene and cresol.

4. The method according to claim 2, wherein the chlorinated aliphatic hydrocarbon compound is at least one compound selected from trichloroethylene and dichloroethylene.

5. A process for remedying an environment contaminated with at least one of an aromatic compound and a chlorinated aliphatic hydrocarbon compound, the environment being at a temperature of between 4 and 15° C., comprising the steps of:
  (a) introducing into the environment a bacterial strain JMC1 (FERM BP-5960), wherein the strain JMC1 is a mutant strain derived from strain JM1 (FERM BP-5352) constitutively expressing oxygenase, and the strain JMC1 has an ability to proliferate on and degrade the aromatic compound and the chlorinated aliphatic hydrocarbon compound constitutively at 4° C.; and
  (b) degrading the aromatic compound or the chlorinated aliphatic hydrocarbon compound employing the strain JMC1 (FERM BP-5960).

6. The method according to claim 5, wherein the environment is contaminated with an aromatic compound.

7. The method according to claim 6, wherein the aromatic compound is at least one compound selected from the group consisting of phenol, toluene and cresol.

8. The method according to claim 5, wherein the environment is contaminated with a chlorinated aliphatic hydrocarbon compound.

9. The method according to claim 8, wherein the chlorinated aliphatic hydrocarbon compound is at least one compound selected from trichloroethylene and dichloroethylene.

10. The method according to claim 5, wherein the environment is an aqueous medium.

11. The method according to claim 10, wherein the aqueous medium is brought into contact with a carrier substance carrying the mutant strain JMC1.

12. The method according to claim 11, wherein the aqueous medium is introduced into a container containing the carrier substance carrying the mutant strain JMC1 through an end of the container and discharging it from an opposite end.

13. The method according to claim 5, wherein the environment is a soil.

14. The method according to claim 13, comprising the steps of: preparing an aqueous medium containing the mutant strain JMC1; and introducing the aqueous medium into the soil.

15. The method according to claim 14, wherein at least one of a nutrient for the mutant strain JMC1 or oxygen is also introduced into the soil.

16. The method according to claim 14, comprising the steps of: installing an injection well into the soil; and introducing the aqueous medium containing the mutant strain JMC1 into the soil through the injection well under pressure.

17. The method according to claim 13, comprising the steps of: placing the mutant strain JMC1 in a liquid; and introducing the soil into the liquid.

18. The method according to claim 5, wherein the environment is a gas.

19. The method according to claim 18, wherein the gas is introduced into a liquid containing the mutant strain JMC1.

20. The method according to claim 18, wherein the gas is brought into contact with a carrier substance carrying the mutant strain JMC1.

21. The method according to claim 18, wherein the gas is introduced into a container containing the carrier substance carrying the mutant strain JMC1 through an end of the container and discharging it from an opposite end.

22. The method according to any one of claims 10, 13 or 18, wherein the environment is contaminated with an aromatic compound.

23. The method according to claim 22, wherein the aromatic compound is at least one compound selected from the group consisting of phenol, toluene and cresol.

24. The method according to any one of claims 10, 13, or 18, wherein the environment is contaminated is with a chlorinated aliphatic hydrocarbon compound.

25. The method according to claim 24, wherein the chlorinated aliphatic hydrocarbon compound is at least one compound selected from trichloroethylene and dichloroethylene.

* * * * *

UNITED STATES PATENT AND TRADEMARK OFFICE
CERTIFICATE OF CORRECTION

PATENT NO.   : 5,962,305
DATED        : October 5, 1999
INVENTOR(S)  : CHIEKO MIHARA ET AL.

It is certified that error appears in the above-identified patent and that said Letters Patent is hereby corrected as shown below:

ON THE TITLE PAGE:

AT [56] REFERENCES CITED

FOREIGN PATENT DOCUMENTS

Insert --0694611  1/96  EPO--.

AT [56] REFERENCES CITED

OTHER PUBLICATIONS

Insert --Leahy, et al.; "Bioremediation: Optimizing Results", Chem. Eng.; 101, 5 (1994) 108-116.--;
　　Insert --Krumme, et al.; "Degradation of Trichloroethylene by *Pseudomonas cepacia* G4 and the Constitutive Mutant Strain G4 5223 PR1 in Aquifer Microcosms"; Appl. & Env. Microb., 59, 8, (1993) pp. 2746-2749.--;
　　Insert --Bradley, et al.; "Rapid Toluene Mineralization by Aquifer Microorganisms at Adak, Alaska: Implications for Intrinsic Bioremediation in Cold Environments, Env. Sci. & Techn., 29, 11 (1995) pp. 2778-2781.--;
　　Insert --Singleton, I.; "Microbial Metabolism of Xenobiotics: Fundamental and Applied Research", J. Chem. Tech. & Biotech., 59, 1, (1994) 9-23.--;
　　Insert --McCarty, et al.; "Ground-Water Treatment for Chlorinated Solvents", Handbook of Bioremediation (1994) 87-116.--;

(continued)

UNITED STATES PATENT AND TRADEMARK OFFICE
CERTIFICATE OF CORRECTION

PATENT NO.    : 5,962,305
DATED         : October 5, 1999
INVENTOR(S)   : CHIEKO MIHARA ET AL.                    Page 2 of 4

It is certified that error appears in the above-identified patent and that said Letters Patent is hereby corrected as shown below:

After Vandenbergh et al., "vol. 54," should read --Appl. & Environ Microbiol., vol. 54,--;
"Munakáta Marr et al." should read --Munakata-Marr et al.-- and
"alsterd" should read --altered--; and
After "Shields, et al., "*Pseudomaonas*" should read --*Pseudomonas*--.

AT [57] ABSTRACT

Line 1, "it" should be deleted.

COLUMN 1

Line 43, "paid" should read --made--.

COLUMN 2

Line 44, "Nelson at al." should read --Nelson et al.--; and
Line 61, "an" should read --a--.

COLUMN 6

Line 11, "the" should read --in the--.

UNITED STATES PATENT AND TRADEMARK OFFICE
CERTIFICATE OF CORRECTION

PATENT NO. : 5,962,305

DATED : October 5, 1999

INVENTOR(S) : CHIEKO MIHARA ET AL.

It is certified that error appears in the above-identified patent and that said Letters Patent is hereby corrected as shown below:

COLUMN 9

Line 15, "proliferates" should read --proliferate--; and
    Line 17, "Additionally" should read --Additionally,--.

COLUMN 11

Line 20, "plate" should read --plates--; and
    Line 41, "were" should read --was--.

COLUMN 12

Line 55, "inoculated." should read --was inoculated.--.

COLUMN 13

Line 31, "While," should read --Next,--.

COLUMN 14

Line 3, "time;" should read --time:--.

COLUMN 15

Line 38, "degrades" should read --degrade--; and
    Line 46, "and" (first occurrence) should be deleted.

UNITED STATES PATENT AND TRADEMARK OFFICE
CERTIFICATE OF CORRECTION

PATENT NO.    : 5,962,305

DATED         : October 5, 1999

INVENTOR(S)   : CHIEKO MIHARA ET AL.

It is certified that error appears in the above-identified patent and that said Letters Patent is hereby corrected as shown below:

COLUMN 18

Line 2, "is" (second occurrence) should be deleted.

Signed and Sealed this

Eleventh Day of July, 2000

Attest:

Q. TODD DICKINSON

*Attesting Officer*    Director of Patents and Trademarks